(12) United States Patent  (10) Patent No.: US 7,525,661 B2
Mandelis et al.  (45) Date of Patent: Apr. 28, 2009

(54) LASER PHOTO-THERMO-ACOUSTIC (PTA) FREQUENCY SWEPT HETERODYNED LOCK-IN DEPTH PROFILOMETRY IMAGING SYSTEM

(76) Inventors: Andreas Mandelis, 3 Scarborough Heights, Toronto, Ontario (CA) M1M 2V3; Alex Vitkin, 130 Glenlake Avenue, Toronto, Ontario (CA) M6P 1E5; Sergey Telenkov, 108 Goodwood Park Crt., Apt.633, Toronto, Ontario (CA) M4C 2H2; Ying Fan, 2505-88 Bloor Street East, Toronto, Ontario (CA) M4W 3G9

( * ) Notice: Subject to any disclaimer, the term of this patent is extended or adjusted under 35 U.S.C. 154(b) by 62 days.

(21) Appl. No.: 11/058,233

(22) Filed: Feb. 16, 2005

(65) Prior Publication Data

US 2005/0234319 A1  Oct. 20, 2005

Related U.S. Application Data

(60) Provisional application No. 60/544,969, filed on Feb. 17, 2004.

(51) Int. Cl.
  *G01B 9/02* (2006.01)
(52) U.S. Cl. .............. 356/432; 356/447; 356/237.1; 356/502
(58) Field of Classification Search .......... 356/432
  See application file for complete search history.

(56) References Cited

U.S. PATENT DOCUMENTS 3,948,345 A * 4/1976 Rosencwaig ............... 73/579
4,255,971 A * 3/1981 Rosencwaig ............... 73/606
6,043,884 A * 3/2000 Curbelo .................... 356/502
6,552,803 B1 * 4/2003 Wang et al. ................ 356/503
2002/0097393 A1 * 7/2002 Nikoonahad et al. ..... 356/237.2
2002/0151798 A1 * 10/2002 Honda ...................... 600/458

OTHER PUBLICATIONS

J. A. Viator, "Characterization of photoacoustic sources in tissue using time domain measurements", Oregon Graduate Institute of Science and Technology, (2001).*

(Continued)

*Primary Examiner*—L. G Lauchman
*Assistant Examiner*—Rebecca C Slomski
(74) *Attorney, Agent, or Firm*—Hill & Schumacher; Lynn C. Schumacher

(57) ABSTRACT

A method and apparatus for biomedical subsurface imaging and measurement of thickness, elastic and optical properties of industrial and biomedical materials based on laser Photo-Thermo-Acoustic (PTA) frequency-swept heterodyne depth profilometry, In particular, the invention relates to biomedical imaging and measure of tissue and tumour thickness, L, speed of sound, $c_s$, acoustic attenuation coefficient, $\gamma$, optical absorption coefficient, $\mu_a$, and optical scattering coefficient, $\mu_s$. The method and apparatus involves providing for a sample of the material to be characterized; irradiating the material for a selected period of time with an excitation waveform from a modulated optical excitation source wherein a photo-thermo-acoustic emission is responsively emitted from said solid; detecting said emitted photo-thermo-acoustic emission; processing the electronic signal to convert the frequency-domain signal into time-domain and perform depth profilometric imaging and determining thermoelastic and optical properties of the material sample.

29 Claims, 13 Drawing Sheets

OTHER PUBLICATIONS

G. Paltauf and H. Schmidt-Kloiber, "Pulsed optoacoustic characterization of layered media", J. Appl. Phys. 88, 1624 (2000).*

Bialkowski, Stephen, Photothermal Spectroscopy Methods for Chemical Analysisi, John Wiley & Sons, Inc., Chapter 1 (1996).*

C.Haisch and R.Niessner, "Light and sound-photoacousitc spectroscocpy", Institute of Hydrochemistry, Technical University of Munich, Marchioninistrasse 17, D-81377 Munich, German, Spectroscopy Europe (2002).*

A. Beenen, G. Spanner and R.Niessner, "Photoacousitc Depth-Resolved Analysis of Tissue Models", Appl Spectrosc 51:51-57 (1997).*

Y. Zeng, D. Xing, Y. Wang, B. Yin, and Q. Chen, "Photoacoustic and ultrasonic coimage with a linear transducer array," Opt. Lett. 29, 1760-1762 (2004).*

A. A. Oraevsky, S. L. Jacques, F. K. Tittel, "Measurement of tissue optical properties by time-resolved detection of laser-induced transient stress," Applied Optics,36, 402-415 (1997).*

* cited by examiner

LASER PHOTO-THERMO-ACOUSTIC (PTA) FREQUENCY SWEPT HETERODYNED LOCK-IN DEPTH PROFILOMETRY IMAGING SYSTEM

We claim the benefit of the priority date Feb. 17, 2004 as per provisional patent application No. 60544969.

TECHNICAL FIELD

The present invention relates to methodology and instrumentation development, in laser Photo-Thermo-Acoustic (PTA) frequency-swept heterodyne depth profilometry, for biomedical subsurface imaging and measurement of thickness, elastic and optical properties of industrial and biomedical materials. In particular, the invention relates to biomedical imaging and measurement of tissue and tumour thickness, L, speed of sound, $c_s$, acoustic attenuation coefficient, $\gamma$, optical absorption coefficient, $\mu_a$, and optical scattering coefficient, $\mu_s$.

BACKGROUND OF INVENTION

The photoacoustic (PA), or more precisely, the photo-thermo-acoustic (PTA) effect is the process of light being absorbed by a material, creating a temperature change followed by a localized volume expansion leading to the generation of acoustic waves. In addition to obvious applications in the area of sub-surface depth profilometry of defects in materials (see Mandelis in Progress in Photothermal and Photoacoustic Science and Technology, North-Holland, New York, 1992), there have been many advances in applying photoacoustic phenomena to soft tissue imaging, cancerous lesion detection, and sub-dermal depth profilometry in the last decade. In recent years, application of laser photoacoustic to soft tissue imaging, cancerous lesion detection, and sub-dermal depth profilometry has enjoyed very rapid development (see A. A. Oraevsky in *Biomedical Optoacoustics*, Proc. SPIE Vol. 3916 and Vol. 4256 and A. J. Welch and M. C. van Gemert in *Tissue Optical Properties and Laser-Tissue Interactions*, AIP, New York, 1995), becoming the object of broader attention by the biomedical optics community (see *Biophotonics International*, September/October 2000, pp. 40-45). This is so because PA detection has shown concrete promise of depth profilometric imaging in turbid media at depths significantly larger than accessible by purely optical methodologies (See V. G. Andreev, A. A. Karabutov, S. V. Solomatin, E. V. Savateeva, V. Aleynikov, Y. Z. Zhulina, R. D. Fleming, and A. A. Oraevsky in *Biomedical Optoacoustics*, Proc. SPIE Vol. 3916). In state-of-the-art laser PA instrumentation and measurement systems in turbid media, as developed by some of the major research groups in this field (see V. G. Andreev, A. A. Karabutov, S. V. Solomatin, E. V. Savateeva, V. Aleynikov, Y. Z. Zhulina, R. D. Fleming, and A. A. Oraevsky in *Biomedical Optoacoustics*, Proc. SPIE Vol. 3916; G. A. Hoelen, R. G. M. Kolkman, M. Letteboer, R. Berendsen and F. F. de Mul in *Optical Tomography and Spectroscopy of Tissue III*, Proc. SPIE Vol. 3597, pp 336; P. C. Beard and T. N. Mills in Proc. SPIE Vol. 3916, pp. 100; L. H. Wang, S. L. Jacques and X. Zhao in Opt. Lett. 20, 629, 1995; G. Yao and L. H. Wang in Appl. Opt. 39, pp. 659), a pulsed laser has always been the source of choice for optical generation of PA signal. The major reasons for this choice are two: a) Following optical absorption of a short laser pulse by turbid tissue, optical-to-thermal energy conversion and localized PTA volume expansion, an acoustic transient received within approximately 1 μs after the end of the laser pulse is essentially thermally adiabatic: it carries information about the thermal shape of the absorber, which substantially coincides with its geometric shape before any significant heat conduction can deform the image at later times (see A. A. Karabutov, N. B. Podymova and V. S. Letokhov in Appl. Opt. 34, pp. 1484); b) In pulsed photoacoustics, a large amount of the available energy is imparted to the Fourier spectral components of the PTA signal response, which correspond to the early-times (or high frequencies) after the arrival of the acoustic pulse at the transducer, thus yielding acceptable signal-to-noise ratios under co-added transient pulse detection (see A. Mandelis in Rev. Sci. Instrum. 65, pp. 3309). Pulsed PTA detection, however, presents disadvantages in terms of laser jitter noise, acoustic and thermal noise within the wide bandwidth of the transducer, hard-to-control depth localization of the contrast-generating sub-surface features, as well as strong background signals from sound scattering tissues. These mechanisms tend to limit system detectivity and signal-to-noise ratio (SNR) and amount to important limitations because they may seriously compromise the contributions to the signal of contrast-generating subsurface features and thus limit the ability to monitor nascent and small size tumors by the PTA technique. In addition, very large pulsed-laser peak fluences incident on living tissue may have detrimental effects and for this reason average pulse energies are very low (<5 mJ) resulting in poor SNR. Besides, it is difficult to construct linear, low-noise detection systems for wide range of pulsed amplitudes, a common requirement for patient-specific diagnostics and laser therapy. Normally, acoustic responses from turbid media are time-gated and Fourier transformed into the frequency domain in order to determine and match the peak response of the transducer with the frequency contents of the PTA signal (see A. Oraevsky and A. Karabutov in *Biomedical Optoacoustics*, Proc. SPIE Vol. 3916, pp 228). Quantitatively, tissue inhomogeneity parameter measurements are derived from the peak of the frequency spectrum of the transformed signal.

Frequency-domain (FD) PTA methodologies can offer alternative detection and imaging schemes with concrete advantages over pulsed laser photoacoustics. These advantages include: a) Low fluence of the harmonic or frequency-swept (chirped) laser modulation, with the concomitant advantage of a much higher tissue damage threshold. A combination of harmonically modulated and chirped detection methodologies (see A. Mandelis in Rev. Sci. Instrum. 65, pp. 3309) can overcome the possible disadvantage of lower signal levels under single-frequency harmonic modulation at high, thermally adiabatic, frequencies (~ MHz), while retaining the speed and wide temporal range of pulsed laser responses. The superior signal-to-noise ratio of the ultra-narrow lock-in amplifier band-pass filter can offset much of the SNR deterioration at MHz frequencies. Frequency chirps, may also recover the strength of the high-frequency Fourier components through fast-Fourier transformation of the frequency-domain transfer function to time-domain impulse-response, thus matching the major advantage of pulsed-laser excitation; b) Depth profilometry over very wide range of frequencies. The depth range in turbid media depends on the acoustic velocity and the optical extinction coefficient at the probe wavelength; c) Possible parallel multi-channel lock-in signal processing and image generation in quasi-real time (see D. Fournier, F. Charbonnier and A. C. Boccara in French Patent 2666, 1993 and J. Selb, S. Leveque-Fort, L. Pottier and C. Boccara in *Biomedical Optoacoustics II*, Proc. SPIE Vol. 4256); d) A substantially wider signal dynamic range through use of lock-in filtering; and e) A simple instrumental normalization procedure through division with a reference signal in the frequency-domain, as opposed to non-trivial deconvolution in the time-domain, especially with highly non-linear (e.g. resonant) ultrasonic transducers. Yet, FD and/or hybrid methods have not been pursued historically in biomedical PTA imaging.

Theory: PTA Wave Generation from a Turbid Solid Immersed in a Fluid

FIG. 1 shows the geometry used for the one-dimensional mathematical model. The configuration closely corresponds to the experimental geometry. It contains three coupled layers: the top and bottom layers are composed of a fluid with the middle layer composed of a solid. The top layer is assumed to be semi-infinite fluid and occupies the spatial region $-\infty < z \leq -L$. It has density $\rho_f$ and speed of sound $c_f$. The solid layer has thickness L, density $\rho_s$, speed of sound $c_s$, specific heat at constant pressure $C_{Ps}$, optical absorption coefficient at the laser wavelength $\mu_a$, optical scattering coefficient $\mu_s$, bulk modulus $K_s$ and isobaric volume expansion coefficient $\beta_s$. The bottom layer extends from $0 \leq z < \infty$. The reason for not considering the finite thickness of the bottom layer is that in our experiments no reflections from the fluid-container interface are observed. However, this feature can be readily added as a straightforward extension to the mathematical theory, as it is easily understood by those skilled in the art.

An analytical solution of the coupled PTA problem in the form of spectral integrals can be obtained by converting the time-domain equations to their frequency-domain counterparts using Fourier transformations (FT) (see A. Karabutov and V. Gusev in *Laser Optoacoustics*, AIP Press, New York, 1993 and A. Mandelis, N. Baddour, Y. Cai and R. Walmsley in *J. Opt. Soc. Am. B* (in press)). For a harmonic optical source, the Fourier transform of the radiative transfer equation yields Eq. (1), which is satisfied by the diffuse photon density wave (DPDW, or diffuse radiant energy fluence rate) field (see T. J. Farrell, M. S. Patterson and B. Wilson in *Med. Phys.* 19, pp. 879), $\psi_d$ [Wm$^{-2}$]:

$$\frac{\partial^2}{\partial z^2}\psi_d(z,\omega) - \sigma_p^2 \psi_d(z,\omega) = I_0' e^{-\mu_t(z+L)}, \quad -L \leq z \leq 0 \tag{1}$$

Here a source strength depth distribution is assumed that decreases exponentially into the turbid medium (Bouguet's law) with total attenuation (extinction) coefficient:

$$\mu_t = \mu_s + \mu_a, \tag{2}$$

Also, $$I_0' = -\frac{I_0 \mu_s}{D}\left(\frac{\mu_t + g\mu_a}{\mu_t - g\mu_s}\right) \text{ and } D = \frac{1}{3[\mu_a + (1-g)\mu_s]}, \tag{3}$$

where $I_0$ is the laser fluence, g is the mean cosine of the scattering function of the photon field over all spatial directions described by the solid angle. In view of the almost entirely forward scattering of photons in tissue, g values range between 0.6 and 0.98 (see W. M. Star and J. P. A. Marijnissen in *J. Photochem. Photobiol., B* 1, 149).

The complex diffuse-photon wave number is defined as (see A. Mandelis in *Diffusion-Wave Fields: Mathematical Methods and Green Functions*, Springer-Verlag, New York, 2001, Chap. 10, pp. 663-708):

$$\sigma_p = \sqrt{\frac{1 - i\omega\tau_a}{D_{\text{eff}}\tau_a}} \text{ where,} \tag{4}$$

$$D_{\text{eff}} = vD = \frac{v}{3[\mu_a + (1-g)\mu_s]}, \tau_a = (v\mu_a)^{-1}.$$

Here v is the speed of light ($\approx 10^{10}$ cm/s for light propagating in turbid media); D is the optical diffusion coefficient, in units of length. The general solution of Eq. (1) is:

$$\psi_d(z,\omega) = A_1 e^{\sigma_p(z+L)} + A_2 e^{-\sigma_p(z+L)} + B e^{-\mu_t(z+L)} \tag{5}$$

Constant B can be determined as:

$$B = \frac{I_0'}{\mu_t^2 - \sigma_p^2} \tag{6}$$

Constants $A_1$, and $A_2$ can be solved using the boundary conditions for the DPDW [20]:

$$\psi_d(-L,\omega) - A\frac{\partial}{\partial z}\psi_d(-L,\omega) = -3\mu_s g A I_0 \tag{7}$$

$$\psi_d(0,\omega) - A\frac{\partial}{\partial z}\psi_d(0,\omega) = 3\mu_s g A I_0 e^{-\mu_t(z+L)}$$

where $$A = 2D\left(\frac{1+r_{21}}{1-r_{21}}\right) \equiv 2D\xi \cdot r_{21}$$

is the internal reflectance, defined as the ratio of the upward-to-downward hemispherical diffuse optical fluxes at the boundary.

Therefore, $$A_2 = \frac{F_1(1+A\sigma_p)e^{\sigma_p L} - F_2(1-A\sigma_p)e^{-\sigma_p L}}{(1+A\sigma_p)^2 e^{\sigma_p L} - (1-A\sigma_p)^2 e^{-\sigma_p L}}; \tag{8}$$

$$A_1 = \frac{F_1 - A_2(1+A\sigma_p)}{(1+A\sigma_p)};$$

$$F_1 = 3\mu_s g A I_0 - B(1+A\mu_t);$$

$$F_2 = 3\mu_s g A I_0 e^{-\mu_t L} - B(1-A\mu_t)e^{-\mu_t L}.$$

To complete the solution, the coherent photon-density field, $\psi_c = I_0 e^{-\mu_t(z+L)}$, must be added to the diffuse-photon-density distribution, $\psi_d$. The total photon density field $\psi_t = \psi_d \psi_c$.

In frequency domain, the thermal-wave equation can be written as:

$$\frac{\partial^2}{\partial z^2}\theta_s(z,\omega) - \left(\frac{i\omega}{\alpha_s}\right)\theta_s(z,\omega) = -\frac{\eta_{NR}\mu_a}{\lambda_s}\psi_t(z,\omega), \tag{9}$$

where $\theta_s(z,\omega)$ is the thermoelastic temperature rise above ambient. $\alpha_s$ and $\lambda_s$ are, respectively, the thermal diffusivity and conductivity of the solid medium. The general solution of Equation (9) is:

$$\theta_s(z,\omega) = C_1 e^{-\sigma_s(z+L)} + C_{1b} e^{\sigma_s(z+L)} + C_2 e^{\sigma_p(z+L)} + C_3 e^{-\sigma_p(z+L)} + C_4 e^{-\mu_t(z+L)}. \tag{10}$$

Constants $C_2$, $C_3$, $C_4$ can be solved as:

$$C_2 = \frac{\eta_{NR}\mu_a A_1}{\lambda_s(\sigma_s^2 - \sigma_p^2)}; \qquad (11)$$

$$C_3 = \frac{\eta_{NR}\mu_a A_2}{\lambda_s(\sigma_s^2 - \sigma_p^2)};$$

$$C_4 = \frac{\eta_{NR}\mu_a(B+1)}{\lambda_s(\sigma_s^2 - \mu_t^2)};$$

In the fluid $z \leq -L$ and $z \geq 0$, the temperature field can be written, respectively, as:

$$\theta_f(z,\omega) = Ce^{\sigma_f(z+L)} z \leq -L.$$

$$\theta_f(z,\omega) = C_b e^{-\sigma_f z} z \geq 0. \qquad (12)$$

Constants $C_1$, $C_{1b}$, $C$, $C_b$ can be solved using the boundary conditions of thermal continuity at the fluid/solid interfaces:

$$\theta_f(-L,\omega) = \theta_s(-L,\omega), \qquad (13)$$

$$\lambda_s \frac{\partial}{\partial z}\theta_s(-L,\omega) = \lambda_f \frac{\partial}{\partial z}\theta_f(-L,\omega),$$

$$\theta_f(0,\omega) = \theta_s(0,\omega)$$

$$\lambda_s \frac{\partial}{\partial z}\theta_s(0,\omega) = \lambda_f \frac{\partial}{\partial z}\theta_f(0,\omega)$$

Therefore, (14)

$$C_1 = \frac{-\lambda_f\sigma_f(C_2+C_3+C_4) + \lambda_s(\sigma_p C_2 - \sigma_p C_3 - \mu_t C_4) - \frac{C_{rhs}(\lambda_f\sigma_f - \lambda_s\sigma_s)e^{-\sigma_s L}}{(\lambda_f\sigma_f + \lambda_s\sigma_s)}}{(\lambda_f\sigma_f + \lambda_s\sigma_s) - \frac{(\lambda_f\sigma_f + \lambda_s\sigma_s)^2 e^{-2\sigma_s L}}{(\lambda_f\sigma_f + \lambda_s\sigma_s)}};$$

$$C_{1b} = \frac{C_{rhs} - (\lambda_f\sigma_f - \lambda_s\sigma_s)e^{-\sigma_s L}C_1}{(\lambda_f\sigma_f + \lambda_s\sigma_s)e^{\sigma_s L}}$$

$$C_{rhs} = \lambda_s(\sigma_p C_3 e^{-\sigma_p L} + \mu_t C_4 e^{-\mu_t L} - \sigma_p C_2 e^{\sigma_p L}) - \lambda_f\sigma_f(C_3 e^{-\sigma_p L} + C_4 e^{-\mu_t L} + C_2 e^{\sigma_p L})$$

By introducing in the solid a particle/molecule displacement potential, $\phi_s(z,\omega)$, the coupled wave equations in the solid and fluid can be easily solved. The displacement potential is related to the magnitude of the one-dimensional displacement vector, $U_s(z,\omega)$, as:

$$U_s(z,\omega) = \frac{\partial}{\partial z}\phi_s(z,\omega), \quad -L \leq z \leq 0. \qquad (15)$$

Due to laser PTA excitation by a large spot-size laser beam, further expanded by intra-solid optical scattering, only longitudinal waves are assumed to propagate in an isotropic solid. This assumption allows the use of the Helmholtz equation which is satisfied by the displacement potential, $\phi_s$:

$$\frac{d^2}{dz^2}\phi_s(z,\omega) + k_s^2\phi_s(z,\omega) = \left(\frac{K_s\beta_s}{\rho_s c_s^2}\right)\theta_s(z,\omega), \qquad (16)$$

where $k_s = \omega/c_s$ is the acoustic wavenumber in the solid for small-amplitude acoustic perturbations. The general solution to this equation is:

$$\phi_s(z,\omega) = G_1 e^{ik_s z} + G_2 e^{ik_s z} + G_3 e^{-\sigma_s(z+L)} + G_4 e^{\sigma_p(z+L)} + G_5 e^{-\sigma_p(z+L)} + G_6 e^{-\mu_t(z+L)} + G_9 e^{\sigma_s(z+L)} \qquad (17)$$

Constants $G_3$, $G_4$, $G_5$ and $G_6$ are found to be:

$$G_3 = \frac{K_s\beta_s C_1}{\rho_s c_s^2(\sigma_s^2 + k_s^2)}, \qquad (18)$$

$$G_4 = \frac{K_s\beta_s C_2}{\rho_s c_s^2(\sigma_p^2 + k_s^2)},$$

$$G_5 = \frac{K_s\beta_s C_3}{\rho_s c_s^2(\sigma_p^2 + k_s^2)}$$

$$G_6 = \frac{K_s\beta_s C_4}{\rho_s c_s^2(\mu_t^2 + k_s^2)}$$

$$G_9 = \frac{K_s\beta_s C_{1b}}{\rho_s c_s^2(\sigma_s^2 + k_s^2)}$$

Inside the fluid, since wave sources are of a potential nature, liquid motion will be potential-driven motion. By introducing a scalar potential of the velocity field, $$v(z,\omega) = \frac{\partial}{\partial z}\psi_{fi}(z,\omega), \quad -\infty < z \leq -L,\ 0 \leq z < \infty, \qquad (19)$$

where the subscript i=1, 2 indicates the top and bottom fluid, respectively, one can obtain the photo-thermo-acoustic wave equation (Eq. (20)) for a non-viscous fluid:

$$\frac{d^2}{dz^2}\psi_{fi}(z,\omega) + k_f^2\psi_{fi}(z,\omega) = 0 \qquad (20)$$

where $k_f = \omega/c_f$ is the wavenumber for small-amplitude acoustic perturbations in the fluid.

The small-amplitude pressure change in the fluid is related to the velocity potential, $\Psi_{fi}$ by:

$$P(z,\omega) = -i\omega\rho_f\psi_{fi}(z,\omega). \qquad (21)$$

The general solutions to Equation (20) can be written as:

$$\psi_{f1}(z,\omega) = G_7 e^{ik_f(z+L)}, \quad -\infty < z \leq -L$$

$$\psi_{f2}(z,\omega) = G_8 e^{ik_f z}, \quad 0 \leq z < \infty \qquad (22)$$

The constants ($G_1$, $G_2$, $G_7$, $G_8$) in equations (17) and (22) can be determined through the boundary conditions of stress and velocity continuity at the two interfaces $z=0$, $-L$.

$$\rho_s c_s^2 \frac{d^2}{dz^2}\phi_s(0,\omega) - K_s\beta_s\theta_s(0,\omega) = -P(0,\omega) = i\omega\rho_f\psi_{f2}(0,\omega), \qquad (23)$$

$$\rho_s c_s^2 \frac{d^2}{dz^2}\phi_s(-L,\omega) - K_s\beta_s\theta_s(-L,\omega) = P(-L,\omega) = i\omega\rho_f\psi_{f1}(-L,\omega),$$

$$i\omega\frac{d}{dz}\phi_s(0,\omega) = \frac{d}{dz}\psi_{f2}(0,\omega),\ i\omega\frac{d}{dz}\phi_s(-L,\omega) = \frac{d}{dz}\psi_{f1}(-L,\omega).$$

Substituting the displacement potential, temperature field, and velocity potentials into the boundary conditions, Eq. (23) can be written as:

$$\begin{bmatrix} A_{11} & A_{12} & A_{13} & A_{14} \\ A_{21} & A_{22} & A_{23} & A_{24} \\ A_{31} & A_{32} & A_{33} & A_{34} \\ A_{41} & A_{42} & A_{43} & A_{44} \end{bmatrix} \begin{bmatrix} G_1 \\ G_2 \\ G_7 \\ G_8 \end{bmatrix} = \begin{bmatrix} H_1 \\ H_2 \\ H_3 \\ H_4 \end{bmatrix}. \quad (24)$$

where $$H_1 = K_s \beta_s (C_1 + C_2 + C_3 + C_4) - \sigma_s^2 \rho_s c_s^2 G_3 - \sigma_p^2 \rho_s c_s^2 G_4 - \sigma_p^2 \rho_s c_s^2 G_5 - \mu_t^2 \rho_s c_s^2 G_6;$$

$$H_2 = K_s \beta_s (C_1 e^{-\sigma_s L} + C_2 e^{\sigma_p L} + C_3 e^{-\sigma_p L} + C_4 e^{-\mu_t L}) - \sigma_s^2 \rho_s c_s^2 e^{-\sigma_s L} G_3 - \sigma_p^2 \rho_s c_s^2 e^{\sigma_p L} G_4 - \sigma_p^2 \rho_s c_s^2 e^{-\sigma_p L} G_5 - \mu_t^2 \rho_s c_s^2 e^{-\mu_t L} G_6;$$

$$H_3 = i\omega(\sigma_s G_3 - \sigma_p G_4 + \sigma_p G_5 + \mu_t G_6);$$

$$H_4 = i\omega(\sigma_s G_3 e^{-\sigma_s L} - \sigma_p G_4 e^{\sigma_p L} + \sigma_p G_5 e^{-\sigma_p L} + \mu_t G_6 e^{-\mu_t L});$$

and $$A_{11} = -\rho_s \omega^2 e^{-ik_s L}; \quad A_{12} = -\rho_s \omega^2 e^{ik_s L}; \quad A_{13} = 0; \quad A_{14} = i\rho_f \omega; \quad (25)$$
$$A_{21} = -\rho_s \omega^2; \quad A_{22} = -\rho_s \omega^2; \quad A_{23} = -i\rho_f \omega; \quad A_{24} = 0;$$
$$A_{31} = -k_s \omega e^{-ik_s L}; \quad A_{32} = k_s \omega e^{ik_s L}; \quad A_{33} = 0; \quad A_{34} = ik_f;$$
$$A_{41} = -k_s \omega; \quad A_{42} = k_s \omega; \quad A_{43} = ik_f; \quad A_{44} = 0.$$

$G_7$, the constant of interest for the fluid pressure field determination, can be solved as:

$$G_7 = \frac{\left(H_1 - \frac{A_{11}c'}{a'}\right)\left(A_{32} - \frac{A_{31}b'}{a'}\right) - \left(H_3 - \frac{A_{31}c'}{a'}\right)\left(A_{12} - \frac{A_{11}b'}{a'}\right)}{A_{14}A_{32} - \frac{A_{14}A_{31}b'}{a'} - A_{34}A_{12} + \frac{A_{34}A_{11}b'}{a'}}, \quad (26)$$

where $a' = A_{21}A_{43} - A_{41}A_{23};$ $b' = A_{22}A_{43} - A_{42}A_{23};$ $c' = A_{43}H_2 - A_{23}H_4.$ The pressure field can then be calculated as:

$$P(z,\omega) = i\omega \rho_f G_7 e^{ik_f(z+L)}. \quad (27)$$

Equation (27) can be used to compute the PTA spectrum within a pre-selected range of modulation frequencies then using inverse Fourier transformation to reproduce the time-domain impulse response. Practical implementation of the PTA technique requires scanning the harmonic modulation frequency over the specified range and may be time-consuming for a wide frequency range. Use of frequency-swept (chirped) modulation signals and heterodyne detection provide a valuable alternative which allows recovery of the PTA spectrum and calculation of the temporal response. Taking into account the time-domain representation of harmonic signals in the form $P(z,t)=P(z,\omega)\exp(i\omega t)$, the acoustic pressure field (27) at the transducer position $z=-L-d$ (where d is the distance between the sample top surface and transducer, i.e. the sample depth) can be written as:

$$P(t)|_{z=-L-d} = i\omega \rho_f G_7 e^{i\omega(t-d/c_f)} \quad (28)$$

When a laser source is modulated by a linear chirp with frequency sweep given by $\omega(t)=a+bt$, where a–initial frequency and b is the sweep rate, the detected pressure wave is:

$$P(t) = -i(a+bt)\rho_f G_7 e^{i[(a+bt)t - a(d/c_f) + \theta]} \quad (29)$$

where the phase $\theta$ is due to the complex valued coefficient $G_7$. The heterodyne signal can be generated by mixing the recorded PTA response with the frequency-swept modulation waveform and suppressing the high-frequency components using a low-pass filter. The resulting product term is:

$$V(t) = P(t) \cdot e^{-i[(a+bt)t]} = -i(a+bt)\rho_f |G_7| e^{-i[(bd/c_f)t + ad/c_f - \theta]} \quad (30)$$

It follows from equation (30), that the resulting heterodyne response is a harmonic signal oscillating at the frequency $f=bd/2\pi c_f$, which depends on the sample depth d. Furthermore, it carries amplitude and phase modulation due to the dependence of the coefficient $G_7$ on frequency $\omega(t)$. Equation (30) relates the spectral content of the heterodyne signal and the depth position of subsurface chromophores generating PTA waves. To improve the SNR of the PTA technique, the heterodyne signal can be measured using a suitable coherent (lock-in) processing algorithm which can be implemented by introducing a variable delay time $\tau$ to the chirped reference waveform and integrating the heterodyne signal over the entire acquisition time interval T:

$$V(\tau) = \int_T P(t) \cdot e^{-i[(a+b(t-\tau))t - a\tau]} dt = \quad (31)$$
$$-i \int_T \omega(t) \rho_f |G_7| e^{i[b(\tau-d/c_f)t + a(\tau - d/c_f) + \theta]} dt$$

Equation (31) indicates that the heterodyne response will differ from zero only when the delay time $\tau$ is equal to the time $d/c_f$, which is the time required for the acoustic waves to propagate a distance d.

In order to uncouple amplitude and phase of the heterodyne signal, the standard quadrature processing algorithm can be applied. It requires two reference waveforms with relative phase shift of $\pi/2$. Then heterodyne signals are formed by mixing both waveforms with the PTA response to determine in-phase $V_1(\tau)$ and out-of-phase $V_2(\tau)$ components according to equation (31). The resulting amplitude A and phase $\theta$ as functions of the delay time $\tau$ can be determined as:

$$A(\tau) = (V_1^2(\tau) + V_2^2(\tau))^{1/2} \quad (32)$$
$$\theta(\tau) = tg^{-1}\left(\frac{V_2(\tau)}{V_1(\tau)}\right)$$

Numerical Results

Theoretical simulations were performed for the simple case of a solid turbid layer immersed in water. Three input parameters, the optical absorption coefficient, optical scattering coefficient and the thickness of the solid were varied independently for each simulation to illustrate the time-domain PTA signal generation through the developed theory. Table 1 (see D. P. Almond and P. M. Patel in *Photothermal Science and Techniques*, Chapman and Hall, 1996 and J. Krautkramer and H. Krautkramer in *Ultrasonic Testing of Materials*, Springer Verlag, 3$^{rd}$ ed., 1983) presents the optical and elastic properties used as input parameters for the mathematical model.

TABLE 1

| Elastic properties used as input parameters for the numerical simulation | | | | |
|---|---|---|---|---|
| $\rho_s$ (kg/m$^3$) | $K_s$ (N/m$^2$) | $\beta_s$ (1/C) | $c_s$ (m/s) | $c_f$ (m/s) |
| 1000 | $0.5 \times 10^3$ | $3.3 \times 10^{-4}$ | 1000 | 1500 |

TABLE 1-continued

Elastic properties used as input parameters for the numerical simulation

| $\rho_f$ (kg/m$^3$) | $\lambda_s$ (W/mK) | $\lambda_f$ (W/mK) | $\alpha_s$ (m$^2$/s) | $\alpha_f$ (m$^2$/s) |
|---|---|---|---|---|
| 998 | 0.55 | 0.61 | $0.12 \times 10^{-6}$ | $0.1 \times 10^{-6}$ |

Equation (27) was used to calculate the laser-induced acoustic field within a user-selected frequency range. The time-domain results were obtained from their frequency-domain counterparts using Inverse Fourier Transformation (IFT). FIGS. 2(a), (b) and (c) illustrate the effects of varying optical absorption (penetration) depth on the PTA signal from a 5-mm thick turbid layer. The two peaks in each plot indicate the acoustic waves generated at the top and bottom surfaces of the turbid layer. It can be observed from these figures that increasing the optical absorption coefficient always results in an increase of the signal amplitudes corresponding to the first peaks. The magnitude of the second peak, however, is affected by the amount of energy transmitted to the bottom of the turbid layer and the amount of energy absorbed by that area. The magnitudes of the peaks in FIG. 2(b) are much larger than those in FIG. 2(a), due to an increase of the optical absorption coefficient, from 0.1 cm$^{-1}$ to 1 cm$^{-1}$. However, FIG. 2(c), which features an optical absorption coefficient of 4 cm$^{-1}$, shows a degraded ratio of the peak magnitudes (second peak/first peak) compare to those of FIGS. 2(a) and 2(b). This indicates that although the optical absorption is higher in FIG. 2(c), significant amount of laser energy is absorbed during the light transmission process, resulting in a smaller amount of optical fluence being available to reach the back surface of the solid.

FIG. 3(a)-(d) feature the same material properties, but with an increased optical scattering coefficient, $\mu_s$, from 0.5 cm$^{-1}$ to 8 cm$^{-1}$. This results in a significant decrease of the acoustic signals (peaks at around 46 μs) at the bottom surface of the turbid layer, which is due to the combined effects of energy absorption and scattering during light transmission. The PTA signals at the top surfaces (peaks at around 39 μs), however, show a slight increase as the scattering coefficient increases. This phenomenon, which is due to the localization of the optical source closer to the surface, is also evident in the experimental results shown in Section C) ii of DETAILED DESCRIPTION OF THE INVENTION.

FIG. 4(a)-(c) show results of numerical calculations of the PTA signal using quadrature detection technique (equations (31) and (32)). In this model, we assumed an optical absorption coefficient of 10 cm$^{-1}$ of a 5 mm thick subsurface layer positioned 5 cm deep, in order to calculate in-phase and out-of-phase heterodyne signals (curves 1 and 2 respectively). Calculation of the amplitude (FIG. 4(b)) shows distinct peaks corresponding to acoustic waves generated at the sample surface and reflected back from the rear interface. The phase plot of the PTA signal shows dramatic changes when delay time corresponds to arrival of acoustic waves.

SUMMARY OF INVENTION

The subject matter of the present invention consists of a novel technique for imaging of biological tissues based on frequency-sweep heterodyne detection, digital signal processing and image reconstruction algorithms, as well as the instrumental hardware configurations employed for acoustic wave generation and detection using photo-thermo-acoustic (PTA) phenomena. The novel PTA imaging technique takes advantage of the direct relationship between propagation delay time of acoustic waves in tissue and spectral content of the heterodyne signal produced by mixing the acoustic response with a linearly frequency-swept modulation waveform. A digital signal processing algorithm is used to identify the coherent PTA response associated with subsurface tissue chromophores.

The instrumental apparatus utilizing PTA imaging technology is designed in two embodiments providing information on PTA heterodyne signal (FIG. 5) as well as amplitude and phase of the coherent photoacoustic response (FIG. 6). Both systems feature frequency-swept (chirped) modulation of a continuous wave (rather than pulsed) laser source at the wavelength 1064 nm within the IR transparency window of human tissue and capable of measuring PTA heterodyne signals signal or time-domain pressure signals utilizing inverse Fourier transformation (IFT). The acoustic wave generation process relies on optical absorption of an intensity-modulated laser beam, fast optical-to-thermal energy conversion, and thermal expansion of the targeted tissues. Therefore, the present heterodyne PTA technique is sensitive to changes in optical absorption cross-section between healthy and malignant tissues, originating from the increased vascularization in the latter.

The present invention also includes a computer program embodied in a computer readable medium for processing frequency-swept acoustic signals, a code segment adapted to compute heterodyne signals for different delay times, a code segment adapted to compute amplitude and phase of the coherent photoacoustic response as well as a code segment adapted to reconstruct two- and three-dimensional images of subsurface tissue chromophores from the recorded frequency-swept photoacoustic signals. The present PTA technique comprising instrumental apparatus and signal processing software constitutes a single embodiment that can be used by a trained operator in clinical settings for rapid examination of tissues (for example, breast tissue) to identify malignant regions from a series of acquired photoacoustic slice images.

Therefore, the present invention provides a method to perform operator-controlled slice-by-slice photo-thermo-acoustic imaging of a material through a coupling fluid, the method comprising the steps of:

(a) irradiating the material at a given point for a selected period of time with an excitation waveform from an optical excitation source modulated by a linear chirp with frequency sweep producing frequency-swept modulation signals wherein frequency-swept photo-thermo-acoustic signals are responsively emitted from said material;

(b) detecting said emitted frequency-swept photo-thermo-acoustic signals;

(c) repeating steps a) and b) while scanning across a surface of the material along a pre-determined line or across a two-dimensional surface area of the material; and (d) electronic signal processing to convert the emitted frequency-domain photo-thermo-acoustic signals into time-domain and perform depth profilometric imaging at each point of the material while scanning to obtain thermoelastic and optical properties of the material at various subsurface depths and producing a two-dimensional slice image of subsurface structures when the scan is along said pre-determined line, or a three-dimensional volume image of subsurface structures when the scan is across said two-dimensional surface area of the sample material.

The present invention also provides an apparatus to perform operator-controlled slice-by-slice photo-thermo-acoustic imaging of a material of interest comprising:

(a) electromagnetic excitation source means modulated by a linear chirp with frequency sweep producing frequency-swept modulation signals for irradiating the material for a selected period of time at a given location on said material;

(b) detection means for detecting frequency-swept photo-thermo-acoustic signals emitted in response to said irradiation;

(c) scanning means for scanning across a surface of the material along a pre-determined line or across a two-dimensional surface area of the material; and (d) processing means configured for performing inverse Fourier transformation (IFR) to convert the emitted frequency-modulated photo-thermo-acoustic signals into time-domain and perform depth profilometric imaging at each point while scanning across said surface to obtain thermoelastic and optical properties of the material at various subsurface depths and producing a two-dimensional slice image of subsurface structures when the scan is along said pre-determined line, or a three-dimensional volume image of subsurface structures when the scan is across said two-dimensional surface area of the sample.

BRIEF DESCRIPTION OF DRAWINGS

The above and further advantages of the invention may be better understood by referring to the following description in conjunction with the accompanying drawings in which corresponding numerals in the various FIGURES refer to the corresponding parts in which.

DETAILED DESCRIPTION OF THE INVENTION

Apparatus

Figure 1:
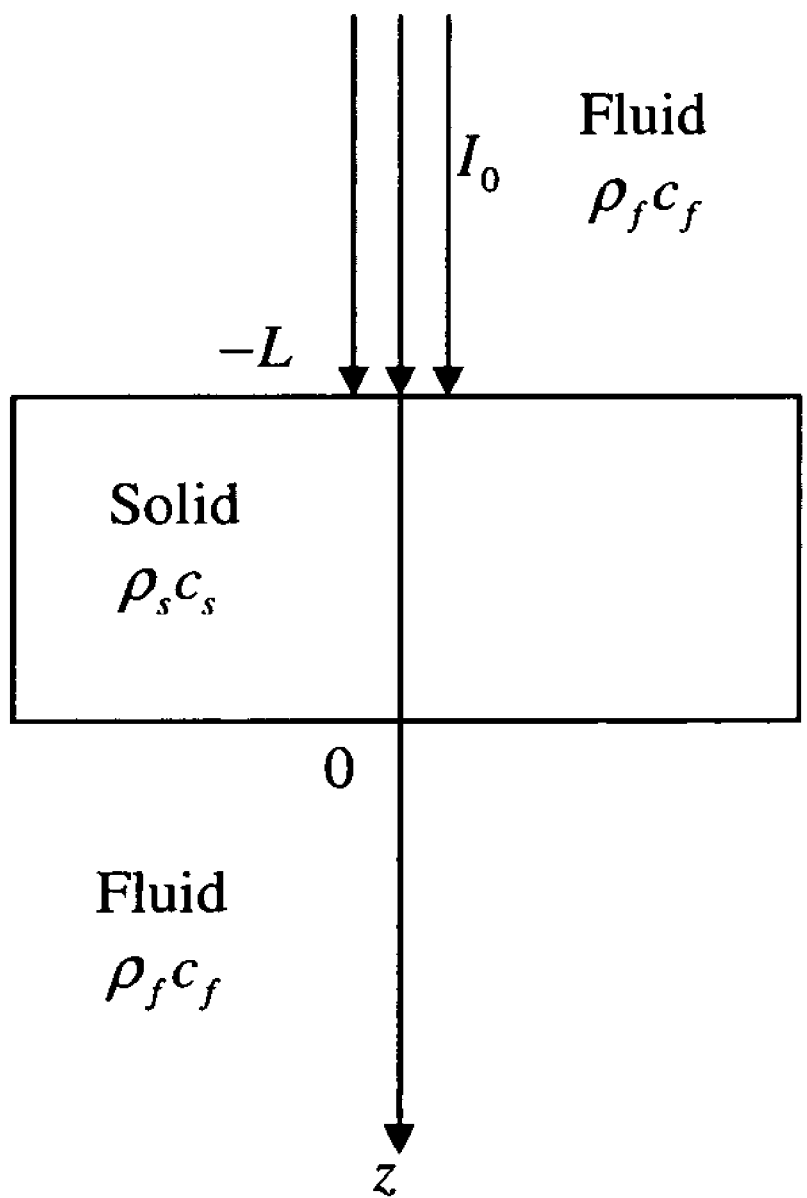
FIG. 1 is a geometry used for formulating the frequency-swept lock-in PTA problem.
Figure 2:
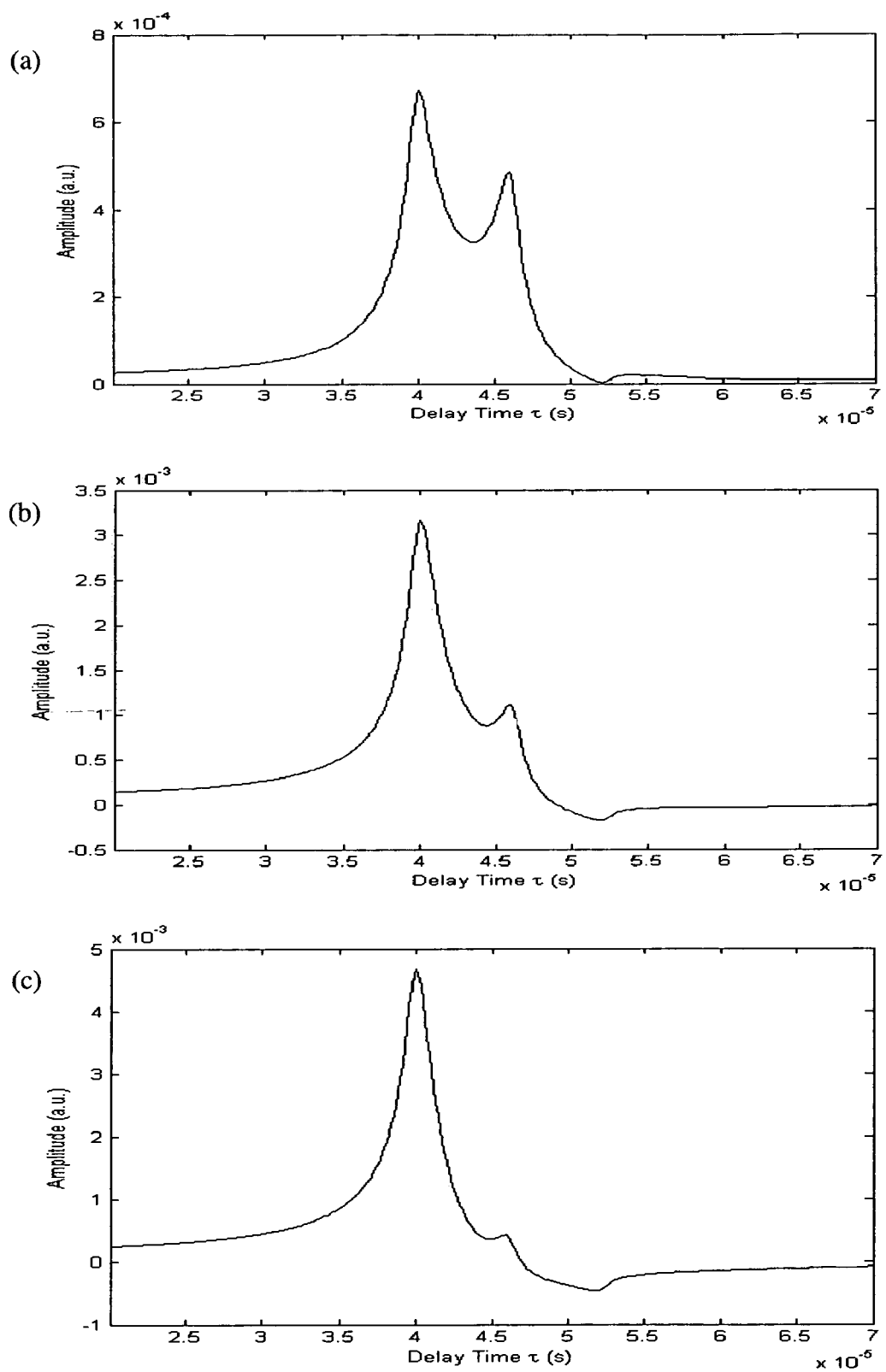
FIG. 2 depicts a simulated PTA field delay-time scan of a solid turbid layer ((a) $\mu_a=10$ m$^{-1}$, $\mu_s=100$ m$^{-1}$; (b) $\mu_a=100$ m$^{-1}$, $\mu_s=100$ m$^{-1}$; (c) $\mu_a=400$m$^{-1}$, $\mu_s=100$ m$^{-1}$). Layer thickness: 5 mm.
Figure 3:
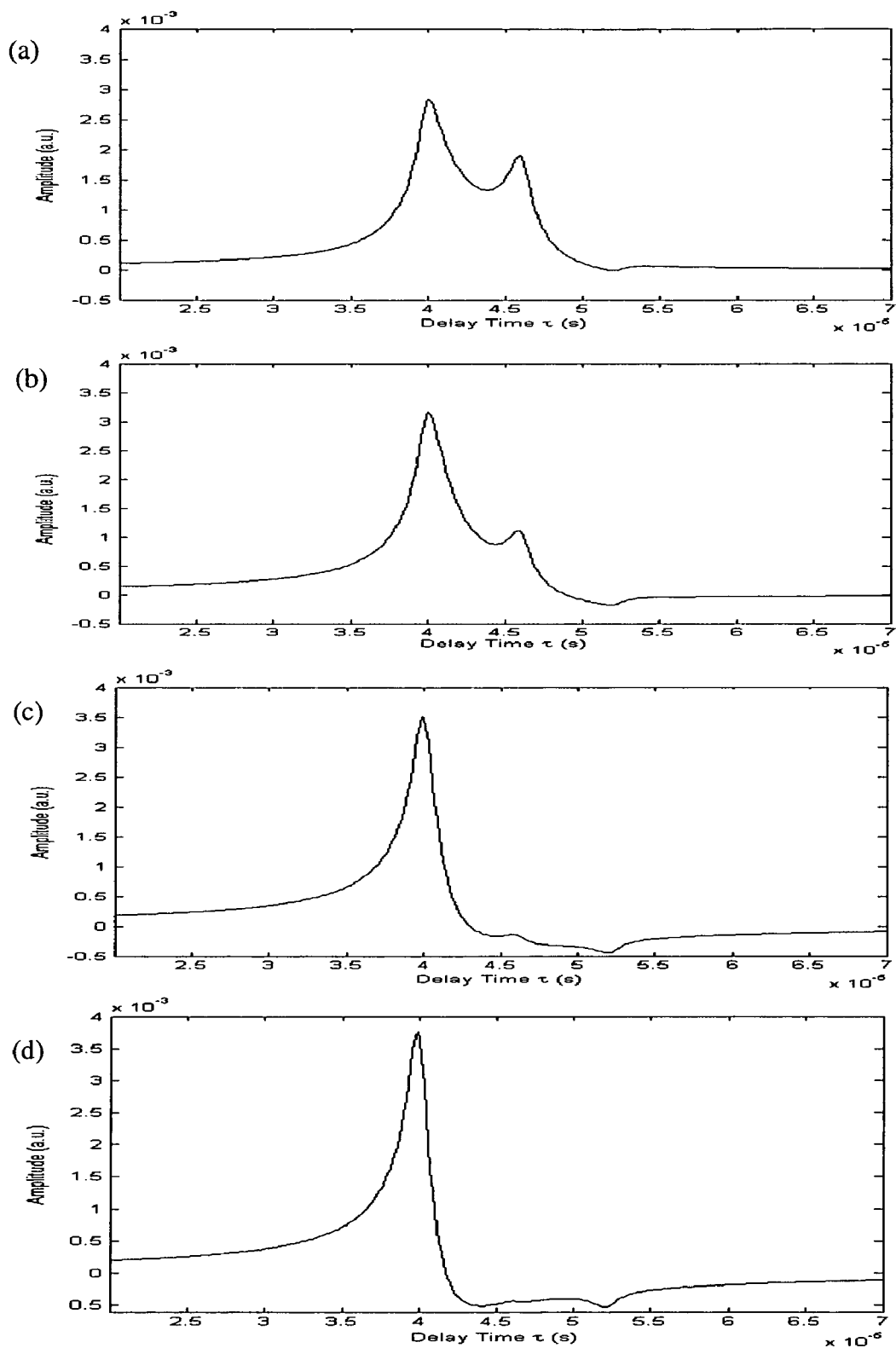
FIG. 3 depicts a simulated PTA field delay-time scan of a solid turbid layer ((a) $\mu_a=100$ m$^{-1}$, $\mu_s=50$ m$^{-1}$; (b) $\mu_a=100$ m$^{-1}$, $\mu_s=100$ m$^{-1}$; (c) $\mu_a=100$ m$^{-1}$, $\mu_s=400$ m$^{-1}$; (d) $\mu_a=100$ m$^{-1}$, $\mu_s=800$ m$^{-1}$). Layer thickness: 5 mm.
Figure 4:
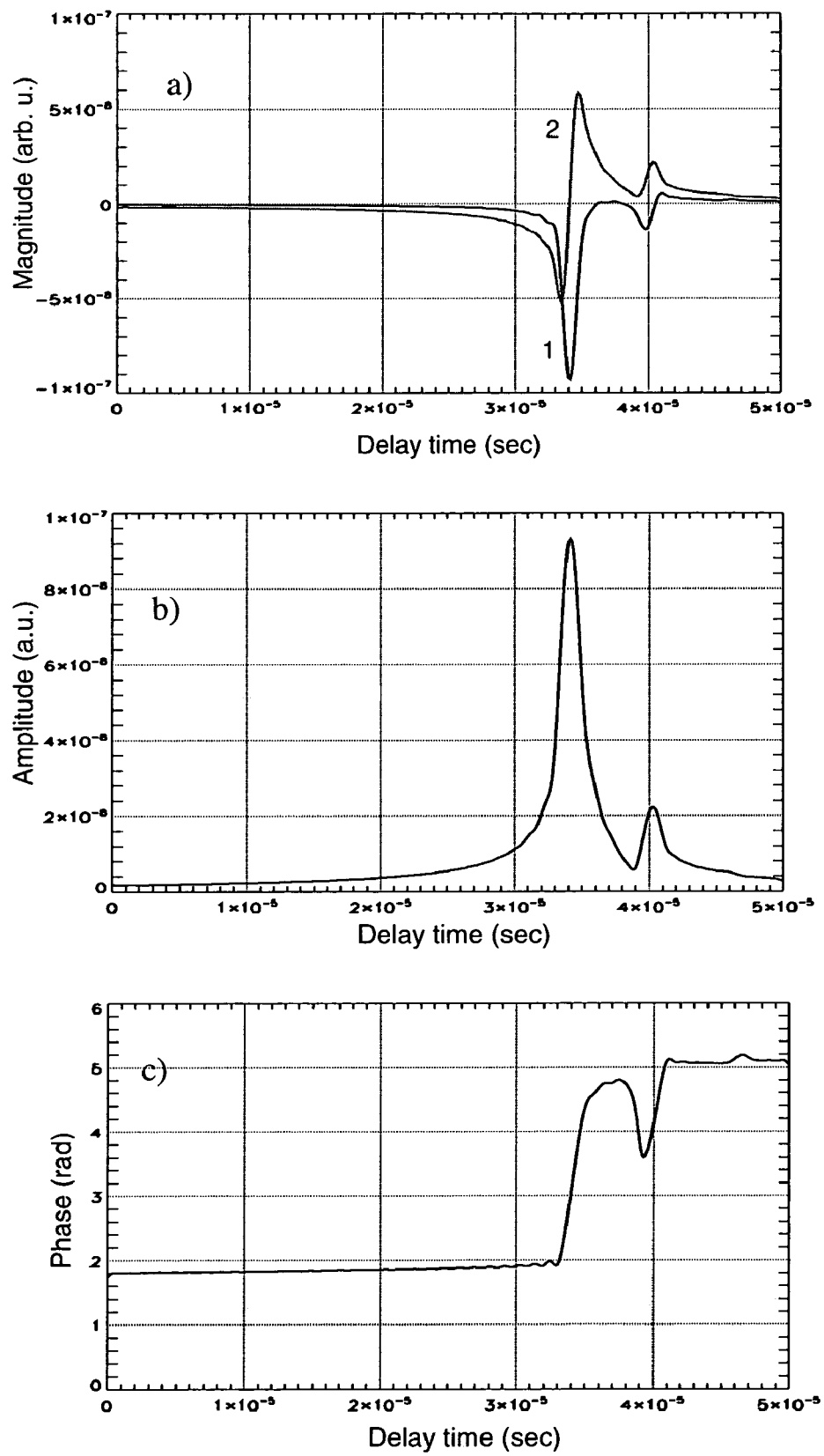
FIG. 4 depicts a simulated in-phase (a, curve 1) and out-of-phase (a, curve 2) components of the PTA signal computed for a subsurface layer with absorption coefficient $\mu_a=10^3$ m$^{-1}$, positioned 5 cm deep. Layer thickness: 5 mm. Simulated amplitude (b) and phase (c) of the PTA signal.
Figure 5:
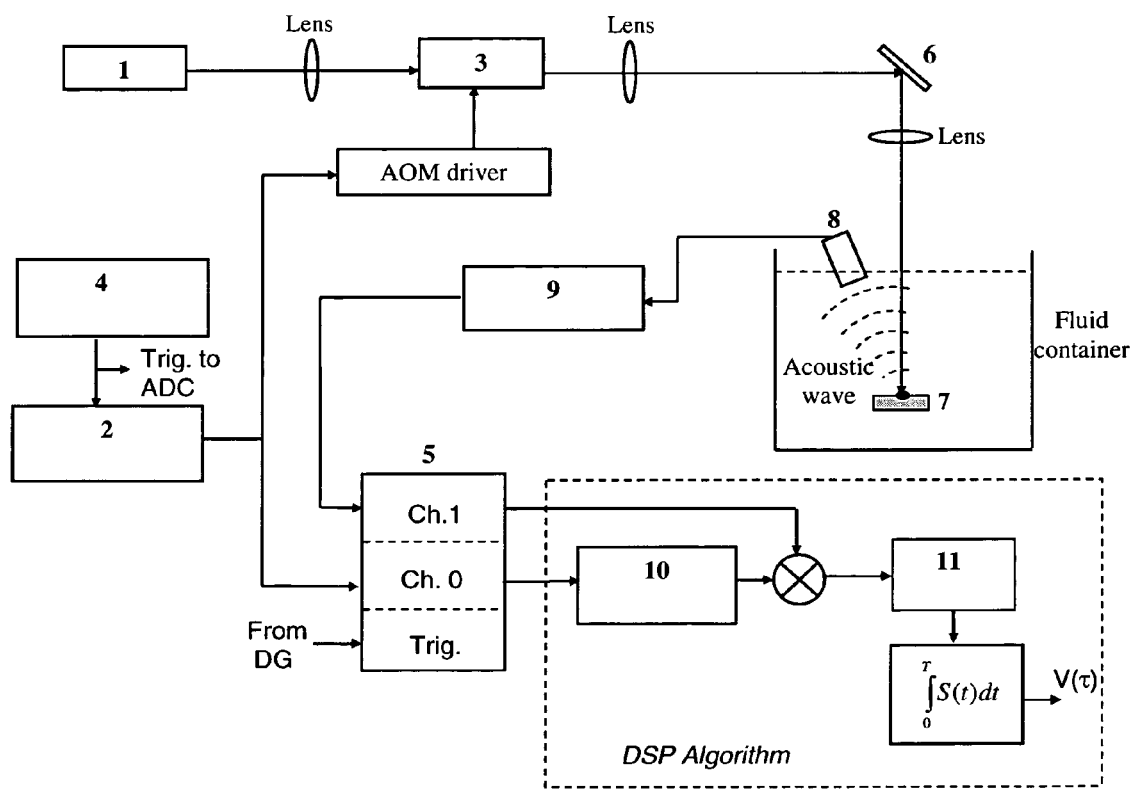
FIG. 5 is a block diagram of one embodiment of the frequency-swept (chirp) heterodyne PTA imaging system.

One embodiment of the frequency-sweep heterodyne PTA imaging system is shown in FIG. 5. The laser used to generate PTA pressure waves is an Ytterbium fiber laser (IPG Photonics, 1064 nm) 1. A frequency-swept (chirp) signal is generated by a function generator (FG, Stanford Research Systems, DS345) 2 to drive the acousto-optic modulator (AOM, Neos Technologies, N15180-1.06-Gap) 3 and modulate the intensity of the laser beam. The chirp signal of FG is triggered by a delay-pulse generator (Stanford Research Systems, DG 535) 4, which is also used to trigger the high-speed analog-to-digital converter (ADC) board (National Instruments, PXI-5122) 5. The laser beam is reflected using an optical mirror 6 and focused onto the specimen 7. A commercial acoustic transducer (Panametrics, V382) 8 is used to detect the acoustical signal. The received signal is amplified by a preamplifier (Panametrics, 5676) 9 and is fed into channel 1 of the ADC board 5. Input channel 0 of the ADC receives the modulation chirp waveform required for digital signal processing (DSP) in a computer program. A segment of computer code 10 introduces a delay time τ to the chirp waveform. Output of the computer code is the product of the delayed (τ) chirp waveform and recorded PTA signal filtered with a software module 11 implementing low-pass filter (LPF) and integrated over the entire acquisition time. The resulting traces of the heterodyne signal as a function of the delay time τ are displayed individually for each experimental setting or merged into a two-dimensional slice or three-dimensional volume images depicting signal dependence on lateral coordinates and depth.

Figure 6:
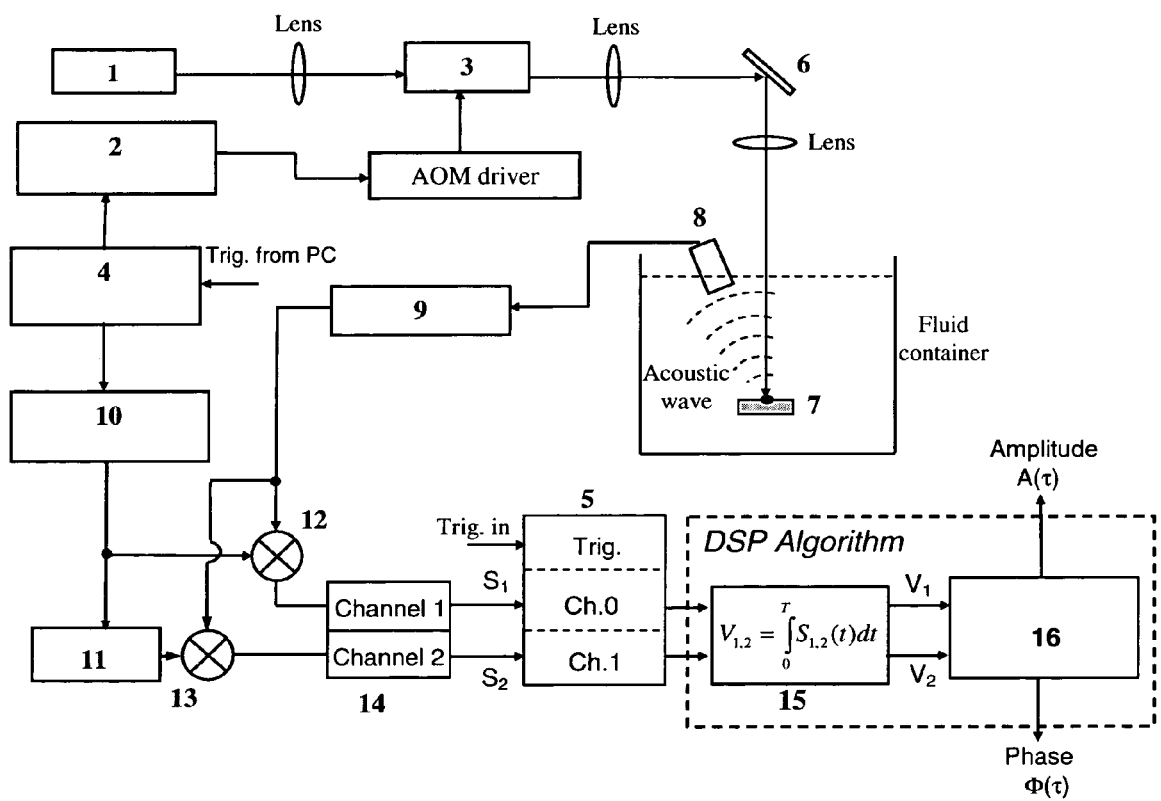
FIG. 6 is a block diagram of another embodiment of the frequency-swept heterodyne PTA imaging system with a quadrature detection technique implemented for amplitude and phase imaging.

The second embodiment of the PTA imaging system is shown in FIG. 6. It utilizes the same optical and electronic instrumentation to generate PTA pressure waves (Ytterbium fiber laser 1, the function generator 2 and acousto-optic modulator 3). Additionally, the second embodiment includes a function generator (FG2, Stanford Research Systems, DS345) 10 to generate a reference signal delayed by τ for the DSP algorithm, and the phase shifting circuit (Pulsar Microwave, QE-19-442) 11 to generate an out-of-phase waveform. Analog mixers (Mini-circuits, ZAD-3) 12, 13 are used to generate simultaneously the products of in-phase and out-of-phase components with the PTA signal which is detected by transducer 8 and amplified using the preamplifier 9. The output signals of the mixers are filtered using the dual-channel low-pass filter (LPF, Stanford Research Systems, SR 640) 14 and then sent to channel 0 and channel 1 of the ADC board 5, where they are digitized and stored in the computer memory. The signal processing algorithm includes integration 15 and computation software modules 16 to determine the signal amplitude A and phase θ versus delay time τ.

PTA Signal Generation

The PTA signal generation associated with the circuit of FIGS. 5 and 6, is possible by means of an intensity modulated laser source. The chirp signal generated by FG can be written as cos [(a+bt)t], where a=1 MHz is the starting frequency and b=4 MHz/ms is the sweep rate. This chirp signal is triggered by the DG 535 delay-pulse generator at the rate 994 Hz. The output of FG drives the acousto-optic modulator and is digitized in the channel 0 of ADC for subsequent signal processing. The intensity of the laser beam is modulated by the AOM according to the chirp signal generated by FG. At the acoustic transducer, the received signal can be written as cos {[a+b(t−d/c$_f$)]t}, where d represents the depth at which the PTA signal originates, and c$_f$ is the speed of sound in the probed medium. Due to the linear relationship between the depth and the delay time when the transducer receives the signal, this expression shows that the information at a certain depth can be related with the frequency components of the chirp signal. Following the amplification stage, the acquired PTA signal is digitized in channel 1 of ADC and saved in the computer memory for further processing. The computer program implementing the DSP algorithm uploads data received in channels 0 and 1, adds delay time τ to the chirped modulation waveform (channel 0) and computes the heterodyne signal using a vector multiplication routine and a low-pass filter to eliminate high-frequency components. The resulting heterodyned signal is integrated over the entire acquisition time to compute the coherent response V(τ). By scanning the chirp delay time, τ, a non-zero signal V(τ) output is expected only when τ=d/cf. Therefore, τ scans at a fixed spatial coordinate are equivalent to depth coordinate scans and can yield information from different probe depths in the sample at a fixed lateral coordinate point. Scanning along a pre-determined line or two-dimensional surface area of the sample, the DSP algorithm generates either a 2-D slice image or 3-D volume image of subsurface structures.

The major difference between the second embodiment of the PTA system, FIG. 6, and the embodiment shown in FIG. 5 is that the delayed chirp signal cos [(a+b(t−τ))t] is generated by function generator FG2 and signal mixing enabled by use of using analog mixers. This scheme allows significant reduction of the sampling rate of the AD converter because, after the low-pass filtering (LPF), the heterodyne signals contain only differential frequency components. Straightforward mathematical operations with digitized in-phase and out-of-phase heterodyne signals allow one to separate amplitude and phase for depth profilometry.

Experimental Results and Discussion

The new PTA imaging system has been characterized using phantoms with tissue-like optical properties. For biomedical imaging, substantial contrast is expected to arise from differences in optical absorptions between healthy and malignant tissue owing to tumour angiogenesis, which gives rise to the presence of increased blood flow in the latter. The optical absorption coefficients at 1064 nm are around 0.1 cm$^{-1}$ and 10 cm$^{-1}$ for blood-deficient dermis and oxygenated blood, respectively (see A. Mandelis in Rev. Sci. Instrum. 65, pp. 3309-3323 and W. M. Star and J. P. A. Marijnissen in *J. Photochem. Photobiol., B* 1, pp. 149). The effective scattering coefficient for breast tissue is around 1.2 cm$^{-1}$ ( see A. J. Welch and M. C. van Gemert in Tissue Optical *Properties and Laser-Tissue Interactions*, AIP, New York, 1995). Solid phantoms were made of plastisol, mixed with different percentages of titanium dioxide and plastic color to closely mimic the scattering and absorption properties of human tissue. Three types of phantom specimens were tested: A) 7.3±1 mm-thick single-layer solid phantoms with varying optical absorption coefficients, μ$_a$, ranging from 0.25 cm$^{-1}$ to 1 cm$^{-1}$; B) 3±0.5 mm thick single-layer solid phantoms with a fixed optical absorption coefficient, μ$_a$=1 cm$^{-1}$, and varying optical scattering coefficients, μ$_s$, ranging from 1 cm1 to 5 cm$^{-1}$; C) an absorbing phantom (μ$_a$=3 cm$^{-1}$) embedded (4 mm deep) inside a scattering medium (μ$_s$=1.3 cm$^{-1}$); D) discrete subsurface chromophores embedded into plastisol substrate with variable thickness and positioned at the different depths. The optical properties of each phantom specimen were obtained from the literature (see D. D. Royston in *J. Biomed. Opt.* 1, pp. 110).

Figure 7:
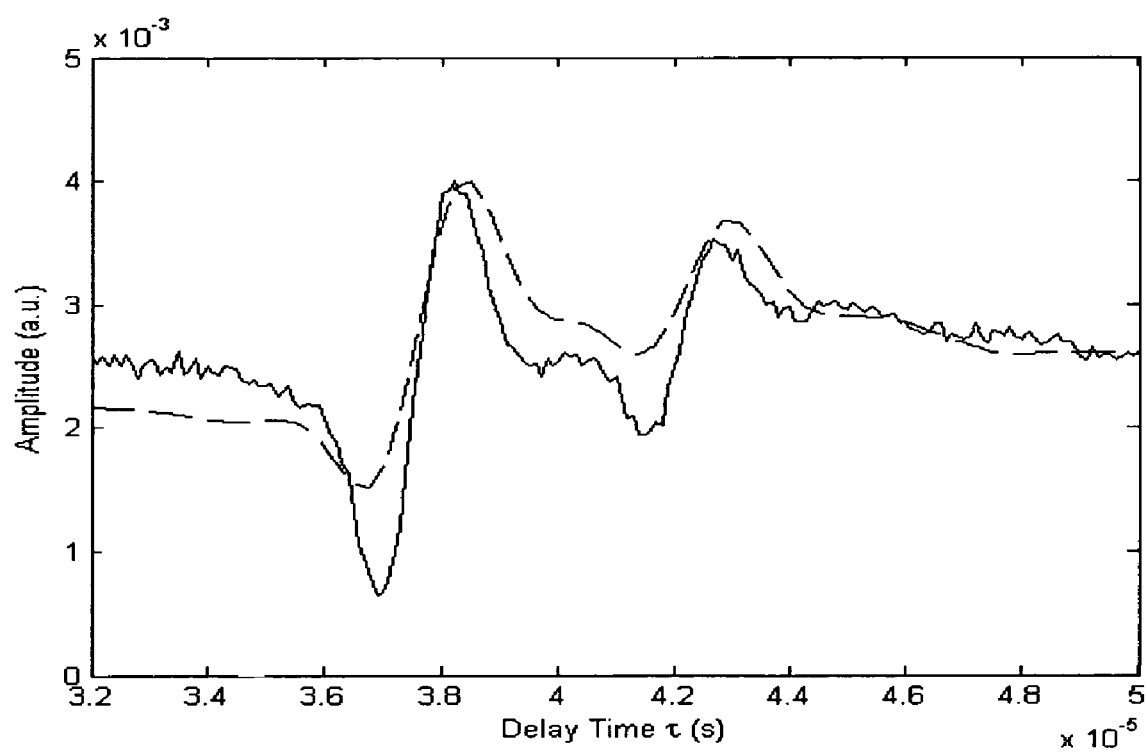
FIG. 7 shows a measured and calculated PTA field delay-time scan obtained from a solid phantom. Fit parameters: sample thickness=6.87 mm, observation distance=54 mm, optical absorption coefficient $\mu_a=95$ m$^{-1}$, optical scattering coefficient $\mu_s=0$ m$^{-1}$. Observation distance is defined as the distance from the acoustic transducer to the top surface of the specimen.
Figure 8:
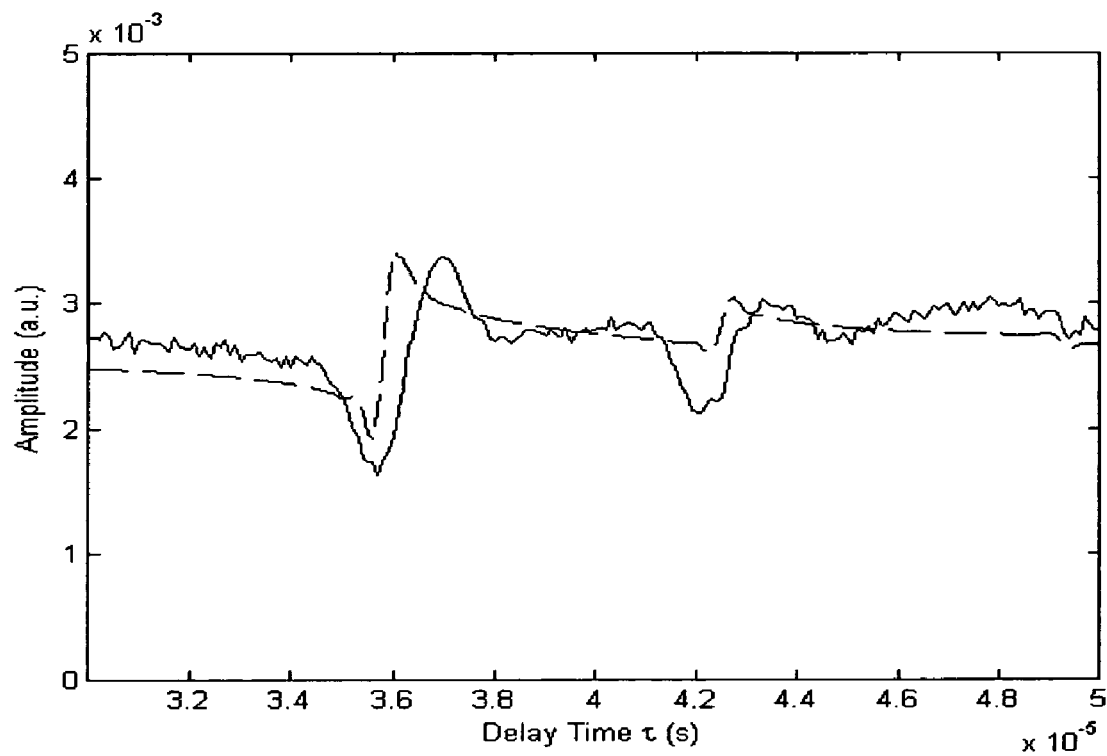
FIG. 8 shows a measured and a calculated PTA field delay-time scan obtained from a solid phantom. Fit parameters: sample thickness=8.2 mm, observation distance=53 mm, optical absorption coefficient $\mu_a=65$ m$^{-1}$, optical scattering coefficient $\mu_s=0$ m$^{-1}$.

The solid lines in FIGS. 7 and 8 are the experimental results of single point scans on type A) specimens, obtained using the PTA imaging system, while the dashed lines are the simulated results. The chirp signal covered a frequency range from 0.1 MHz to 1 MHz and the step size of the delay time used for the scan was 0.1 μs. The frequency-domain simulated results were calculated by substituting the thickness, observation distance (the distance from the acoustic transducer to the top surface of the specimen), material properties, and the chirp frequency range into Equation 27. The corresponding time-domain pressure fields were obtained by applying inverse Fourier transformation to the frequency-domain results. Good agreement was obtained between the experimental and numerical results. Due to the large size of the laser beam (~4 mm) and the short distance from the imaging layer to the interface, the PTA behaviour was expected to be very similar to the 1-D situation and to be adequately interpreted by our 1-D theory, as observed.

To obtain the best fits to the entire frequency record of the pressure responses, the exact values of the bulk modulus, K$_s$, isobaric volume expansion coefficient, β$_s$, thermal diffusivities, α$_{f,s}$, and thermal conductivities, λ$_{f,s}$, were found not to be as important as the speed of sound, sample thickness, observation distance and optical properties of the sample. For the secondary parameters, the listed values in Table 2 were used for the numerical simulations. An important parameter used for the theoretical fits is the speed of sound, c$_s$=1390 m/s, which was obtained using time-of-flight measurements. The other primary parameters, including the optical coefficients, the sample thickness, and the observation distance are listed in the caption of each figure.

TABLE 2

Elastic properties used as input parameters for the mathematical model

| ρ$_s$ (kg/m$^3$) | K$_s$ (N/m$^2$) | β$_s$ (1/C) | c$_s$ (m/s) | c$_f$(m/s) |
|---|---|---|---|---|
| 950 | 0.5 × 10$^3$ | 3.3 × 10$^{-4}$ | 1390 | 1474 |
| ρ$_f$(kg/m$^3$) | λ$_s$ (W/mK) | λ$_f$(W/mK) | α$_s$ (m$^2$/s) | α$_f$(m$^2$/s) |
| 998 | 0.55 | 0.61 | 0.12 × 10$^{-6}$ | 0.1 × 10$^{-6}$ |

Figure 9:
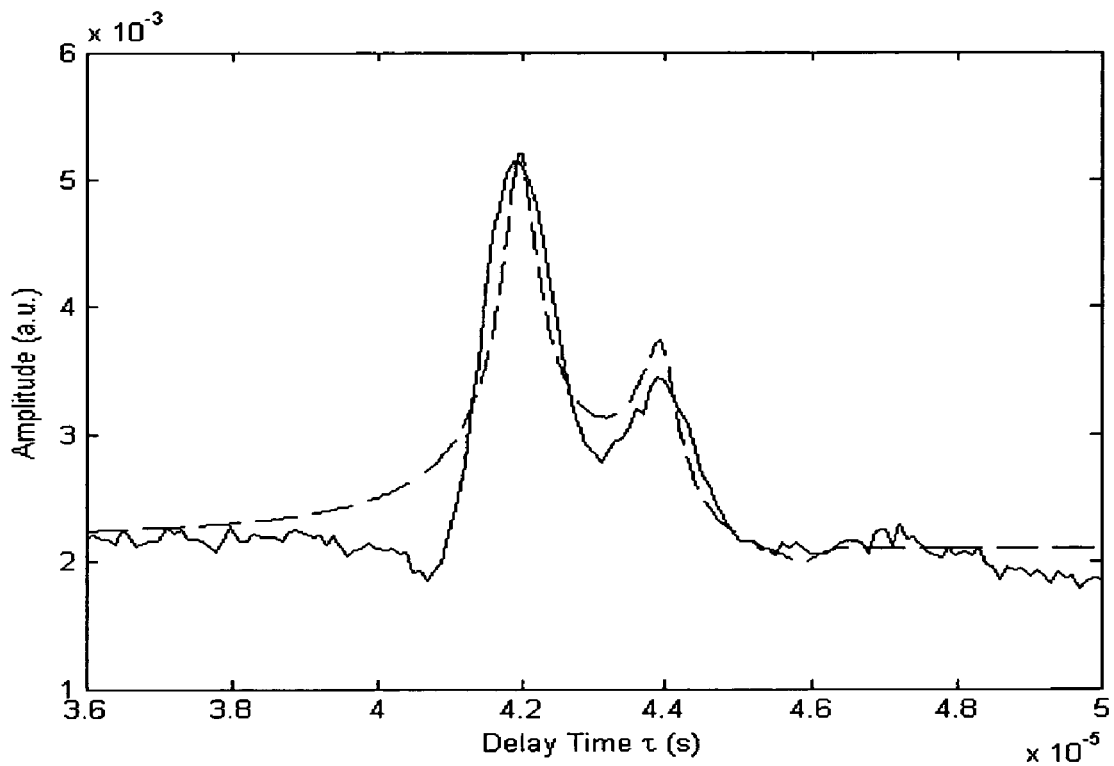
FIG. 9 shows a measured and a calculated PTA field delay-time scan obtained from a solid phantom. Fit parameters: sample thickness=2.87 mm, observation distance=61 mm, optical absorption coefficient $\mu_a=100$ m$^{-1}$, optical scattering coefficient $\mu_s=100$ m$^{-1}$.
Figure 10:
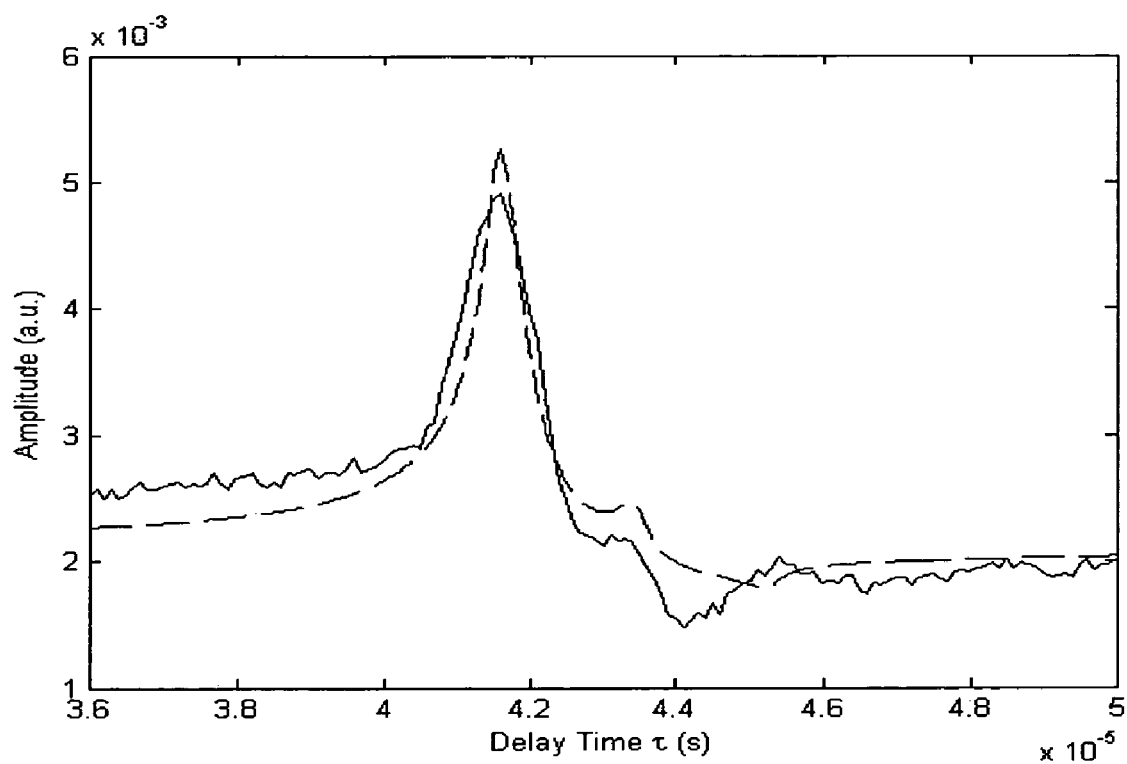
FIG. 10 depicts the measured and calculated PTA field obtained from a solid phantom. Fit parameters: sample thickness=2.85 mm, observation distance=60 mm, optical absorption coefficient $\mu_a=100$ m$^{-1}$, optical scattering coefficient $\mu_s=500$ m$^{-1}$.

The solid lines in FIGS. 9 and 10 are the experimental results of single point scans on type B) specimens, obtained using the PTA imaging system, while the dashed lines are the simulated results. To obtain the best fits to the entire frequency record of the pressure responses, the most important parameters are the speed of sound, sample thickness, observation distance and the optical properties of the sample. Since both type A and type B materials were manufactured using the same material, plastisol, the speed of sound of plastisol, c$_s$=1390 m/s, was used for the numerical curve fitting. The other primary parameters, including the optical coefficients, the sample thickness, and the observation distance are listed in the caption of each figure. The absorption coefficients were obtained using optical measurements and the scattering coefficients were obtained from numerical curve fitting.

Figure 11:
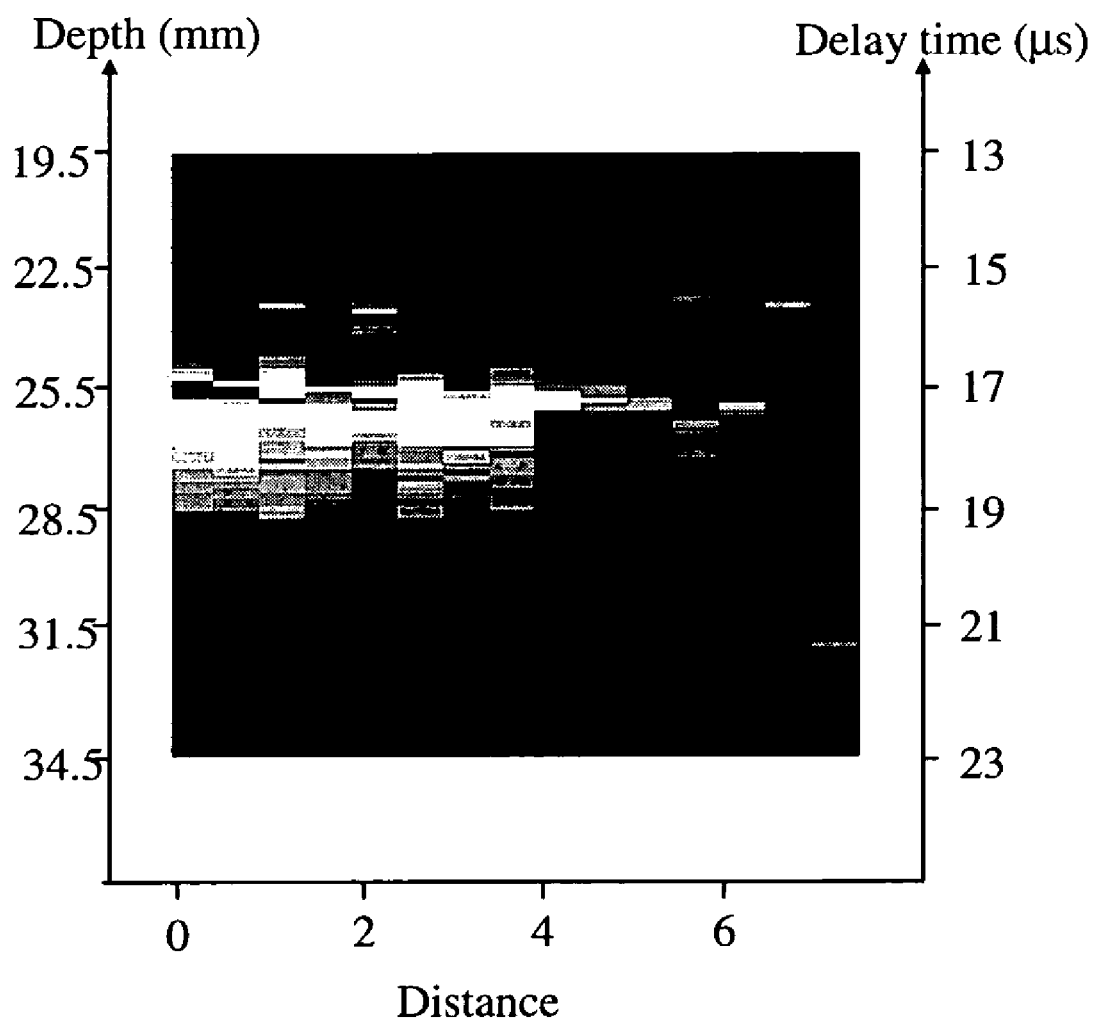
FIG. 11 depicts PTA depth profilometric imaging of an absorber (4 mm wide and 3 mm thick) embedded in a scattering medium. The horizontal pixel size is 0.5 mm and the vertical pixel size is 0.1 μs, which corresponds to a distance of around 150 μm in water.

FIG. 11 shows the depth profilometric image of the cross-section of an absorber (4 mm by 3 mm) embedded in a scattering medium (type C specimen specified above). The right-hand-side vertical axis indicates the time delay and the left hand side vertical axis indicates the equivalent depth. The horizontal axis is the spatial scan coordinate. The range of the delay time is precisely controlled to be 13 μs-23 μs to cover an area of interest (object area). This level of image depth control is a major advantage of this PTA technique compared to conventional pulse-laser diagnostics. The step size of the delay time is 0.1 μs, which corresponds to a distance of around 150 μm in water. The horizontal pixel size is 0.5 mm. The front surface of the absorber is clearly visible with a sharp increase of the PTA signal. The bottom surface of the embedded object is visible, featuring lower signal amplitude, which is due to the attenuation of optical and acoustical energy.

Figure 12:
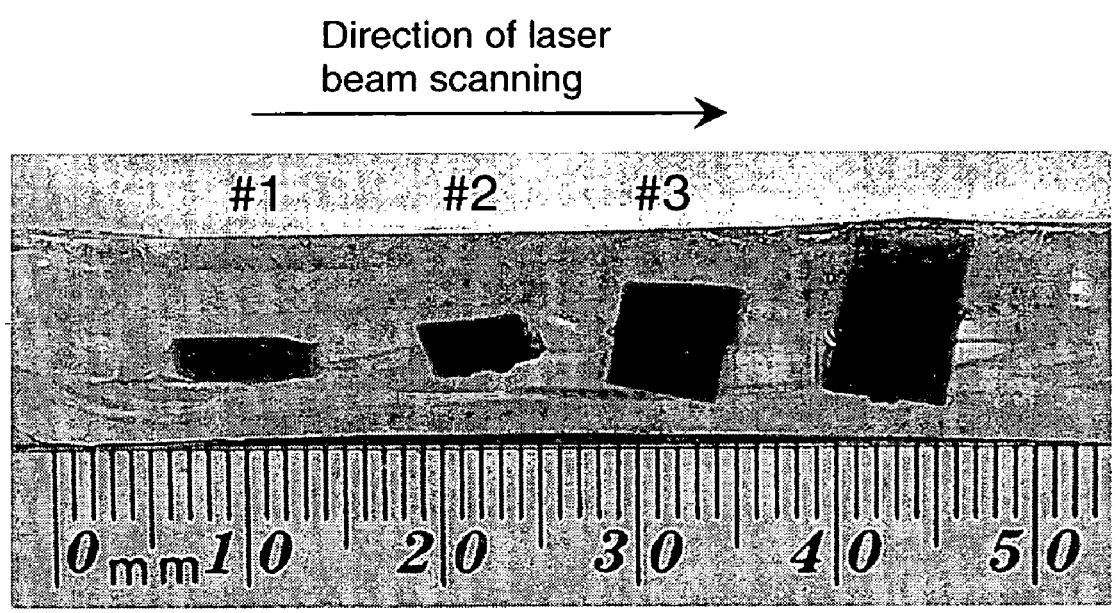
FIG. 12 depicts a cross-sectional optical image of a plastisol test sample with embedded chromophores. The direction of the laser beam scan is also indicated.
Figure 13:
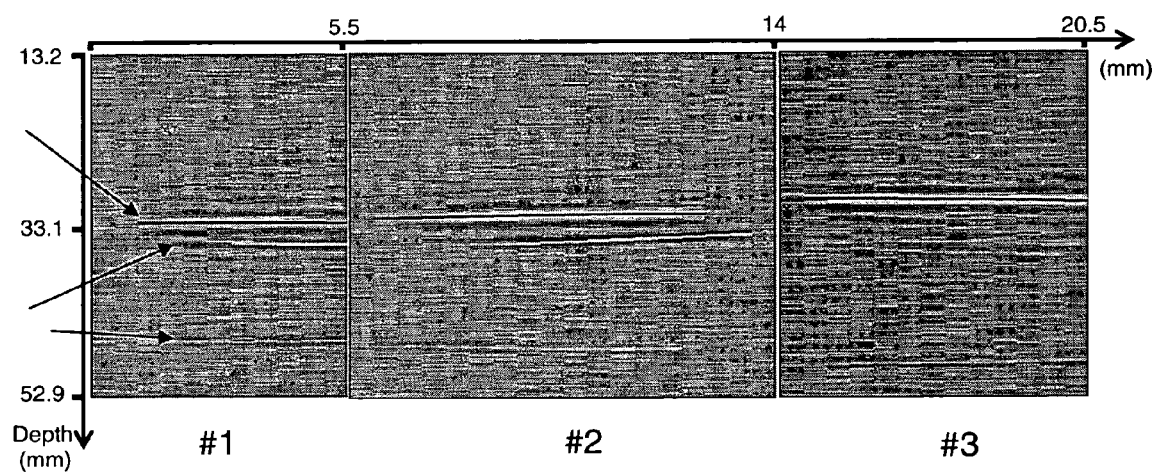
FIG. 13 depicts a two-dimensional PTA slice image of the test sample shown in FIG. 12. Subsurface interfaces generating acoustic waves are marked with arrows. Horizontal pixel size is 0.5 mm.

FIG. 12 depicts an optical cross-section image of the plastisol substrate with embedded discrete chromophores. The PTA signal was recorded during horizontal scans of the laser beam in the direction shown in the Figure. Overall scanning distance exceeded 20 mm to record images of the first three chromophores (#1 through #3). Delay time measurements were converted into depth coordinates using the value of the speed of sound in water $c_f$. The recorded two-dimensional PTA slice-image is shown in FIG. 13. The sharp dark line on all three image segments indicates position of the chromophore top surface where acoustic wave generation occurs. Additionally, the chromophore back surface and the bottom of the plastisol substrate are visible as white lines.

Therefore what is claimed is:

1. A method to perform operator-controlled slice-by-slice photo-thermo-acoustic imaging of a material through a coupling fluid, the method comprising the steps of:
   (a) irradiating the material at a given point for a selected period of time with an excitation waveform from an optical excitation source modulated by a linear chirp with frequency sweep producing frequency-swept modulation signals wherein frequency-swept photo-thermo-acoustic signals are responsively emitted from said material;
   (b) detecting said emitted frequency-swept photo-thermo-acoustic signals;
   (c) repeating steps a) and b) while scanning across a surface of the material along a pre-determined line or across a two-dimensional surface area of the material; and
   (d) electronic signal processing to convert the emitted frequency-domain photo-thermo-acoustic signals into time-domain and perform depth profilometric imaging at each point of the material while scanning to obtain thermoelastic and optical properties of the material at various subsurface depths and producing a two-dimensional slice image of subsurface structures when the scan is along said pre-determined line, or a three-dimensional volume image of subsurface structures when the scan is across said two-dimensional surface area of the sample material.

2. The method according to claim 1 wherein said material includes tissue, biomedical material and industrial material.

3. The method according to claim 1 wherein said excitation source is a continuous-wave laser beam, or any other radiation energy source across the electromagnetic spectrum which can penetrate and be absorbed by said material, resulting in differential absorption and thermoelastic signal contrast between normal and defective or lesion containing region.

4. The method according to claim 1 wherein said excitation source is a semiconductor laser or Ytterbium fiber laser or any other periodically modulated source of electromagnetic radiation, which can produce a photo-thermo-acoustic effect within the spectral window including, but not restricted by, the range of human tissue transmission (650-1064 nm) and beyond into the infrared and microwave spectral range.

5. The method according to claim 1 wherein said excitation source is an array of pulsed semiconductor lasers driven periodically by a driver/power supply with phase synchronizing trigger, so as to deliver at the same spot, or a series of spots while scanning across the surface of the material, a desired summary high power and high repetition rate at an optimally designed repetition period and signal-to-noise ratio, thus circumventing electrical power inductance constraints of high-power and low repetition rate or low power and high repetition rate.

6. The method according to claim 3 wherein said continuous-wave laser is modulated by means of current modulation, an acousto-optic modulator, mechanical chopper, or electro-optic modulator.

7. The method according to claim 1 wherein said optical excitation source is a continuous-wave laser.

8. The method according to claim 1 wherein said step of detecting is done by means of a single-element acoustic detector or multi-element acoustic transducer array.

9. The method according to claim 1 wherein said electronic signal processing is done by a circuit comprising two stages of frequency mixing and low-pass filtering and a lock-in signal detecting circuit.

10. The method according to claim 1 wherein said step of detecting is done by measuring a heterodyne signal produced in the process of mixing a reference signal with acquired acoustic signal.

11. The method according to claim 1 wherein said step of detecting is done by generating quadrature and in-phase reference signals for simultaneous measurements of amplitude and phase.

12. The method according to claim 1 wherein said step of detecting is done by combining individual scans of heterodyne signal, signal amplitude or phase to create said two-dimensional slice image or said three-dimensional volume image of subsurface structures.

13. The method according to claim 1 wherein the thermoelastic properties include speed of sound, $c_s$, and acoustic attenuation coefficient, $\gamma$.

14. The method according to claim 1 wherein the optical properties include optical absorption coefficient, $\mu_a$, and effective optical scattering coefficient, $\mu_s$.

15. The method according to claim 1 wherein said step of detecting includes using a lock-in amplifier.

16. An apparatus to perform operator-controlled slice-by-slice photo-thermo-acoustic imaging of a material of interest through a coupling fluid, comprising:
   (a) electromagnetic excitation source means modulated by a linear chirp with frequency sweep producing frequency-swept modulation signals for irradiating the material for a selected period of time at a given location on said material;
   (b) detection means for detecting frequency-swept photo-thermo-acoustic signals emitted in response to said irradiation;
   (c) scanning means for scanning across a surface of the material along a pre-determined line or across a two-dimensional surface area of the material; and
   (d) processing means configured for performing inverse Fourier transformation (IFR) to convert the emitted frequency-modulated photo-thermo-acoustic signals into time-domain and perform depth profilometric imaging at each point while scanning across said surface to obtain thermoelastic and optical properties of the material at various subsurface depths and producing a two-dimensional slice image of subsurface structures when the scan is along said pre-determined line, or a three-dimensional volume image of subsurface structures when the scan is across said two-dimensional surface area of the sample.

17. The apparatus according to claim 16 wherein said material is tissue, biomedical material or industrial material.

18. The apparatus according to claim 16 wherein excitation source is a continuous-wave laser beam.

19. The apparatus according to claim 16 wherein said excitation source is modulated by an acousto-optic modulator or a power driver with a phase synchronizing unit to simultaneously trigger the firing of an array of pulsed lasers with pre-determined high repetition rate (equivalent to modulation frequency in the kHz-MHz range) or repetition period range (equivalent to chirped modulation) and optimal combined high peak power.

20. The apparatus according to claim 16 wherein said detection means is a single-element or multi-element acoustic transducer.

21. The apparatus according to claim 16 wherein said processing means includes a circuit comprising first and second stages of frequency mixing and low-pass filtering, wherein at said first mixing/low-pass filtering stage two input signals include an acoustic signal detected by an acoustic receiver and a linear frequency sweep modulated electronic signal generated by a function generator, and at said second mixing and low-pass filtering stage, two input signals include an output signal from the first mixing/low-pass filtering stage and a single frequency harmonic signal generated by an internal oscillator of a lock-in amplifier.

22. The apparatus according to claim 16 wherein said detection means includes a lock-in amplifier.

23. The apparatus according to claim 16 wherein said detection means includes means for measuring heterodyne signal produced in hardware or software modules by mixing a reference and acquired signals.

24. The apparatus according to claim 16 wherein said detection means includes means for using quadrature and in-phase reference signals produced in hardware or software modules.

25. The apparatus according to claim 16 wherein the thermoelastic properties include speed of sound, $c_s$, and acoustic attenuation coefficient, $\gamma$.

26. The apparatus according to claim 16 wherein the optical properties include optical absorption coefficient, $\mu_a$, and effective optical scattering coefficient, $\mu_s$.

27. The method according to claim 3 wherein said excitation source is microwave or millimeter wave radiation.

28. The method according to claim 1 wherein said step d) of converting said emitted frequency-domain photo-thermo-acoustic signals into time-domain and perform depth profilometric imaging at each point includes introducing a variable delay time, $\tau$, to a chirped reference waveform used for producing said frequency-swept modulation signals, and wherein a heterodyne response will differ from zero only when the delay time $\tau$ is equal to a time given by $d/c_f$, which is a time required for acoustic waves to propagate a distance d, where $c_f$ is speed of sound in the fluid.

29. The apparatus according to claim 16 wherein said processing means is configured for performing said inverse Fourier transformation (IFR) to convert the emitted frequency-modulated photo-thermo-acoustic signals into time-domain by introducing a variable delay time, $\tau$, to a chirped reference waveform used for producing said frequency-swept modulation signals, and wherein a heterodyne response will differ from zero only when the delay time $\tau$ is equal to a time given by $d/c_f$, which is a time required for acoustic waves to propagate a distance d, where $c_f$ is speed of sound in the fluid.

* * * * *